United States Patent [19]

Moriyama et al.

[11] 4,082,089
[45] Apr. 4, 1978

[54] MASSAGING INSTRUMENT AND A MASSAGING ASSEMBLY

[76] Inventors: Hisa Moriyama; Toshiyuki Moriyama, both of Nouman 1531, Ichihara-shi, Chiba-ken, Japan

[21] Appl. No.: 739,737

[22] Filed: Nov. 8, 1976

[51] Int. Cl.² ............................................. A61H 29/00
[52] U.S. Cl. ................................................ 128/24.3
[58] Field of Search .................. 128/24.1, 24.2, 67, 128/24.3, 399, 254, 255

[56] References Cited

U.S. PATENT DOCUMENTS

| | | | |
|---|---|---|---|
| 547,076 | 10/1895 | Hubbell | 128/24.1 |
| 1,628,272 | 5/1927 | Reitz | 128/24.2 |
| 1,844,247 | 2/1932 | Freemon | 128/24.2 |
| 3,168,895 | 2/1965 | Okuhara | 128/399 |
| 3,382,866 | 5/1968 | Harris | 128/24.3 |

*Primary Examiner*—Lawrence W. Trapp
*Attorney, Agent, or Firm*—Martin A. Farber

[57] ABSTRACT

A massaging instrument for use in beauty art, and particularly to a massaging instrument which gives thermal stimulation to human skins.

4 Claims, 6 Drawing Figures

MASSAGING INSTRUMENT AND A MASSAGING ASSEMBLY

BACKGROUND OF THE INVENTION

In beauty art, it is known that human skins are dipped in moderately hot water and/or a cold water and thereafter massaged whereby relative good massaging effect is attained.

This massaging method, however, is troublesome because of needing somewhat long time for the preparation of hot and cold waters. Further, since the temperature of the hot water is limited to a certain value, that is, room temperature plus 20° C, thermal stimulation obtained by this method is lower than a desired level. If the temperature of the hot water is too high, a woman will suffer from scald.

SUMMARY OF THE INVENTION

An object of this invention is to provide a massaging instrument free from such defects as mentioned above.

Another object of this invention is to provide a massaging instrument which is very conveniently used and can give sufficiently thermal stimulation to human skins.

The above-mentioned objects of this invention is attained by a massaging instrument comprising a grippable support member, a first massaging means which is mounted to said support member and heated to give hot thermal stimulation to human skins and a second massaging means which is mounted to said support member and cooled to give cold thermal stimulation to human skins. Other objects and advantages of this invention will be understood the explanation of this invention referring to embodiments.

DETAILED DESCRIPTION OF THE INVENTION

This invention will be explained hereinafter referring to accompanied drawings.

Figure 1:
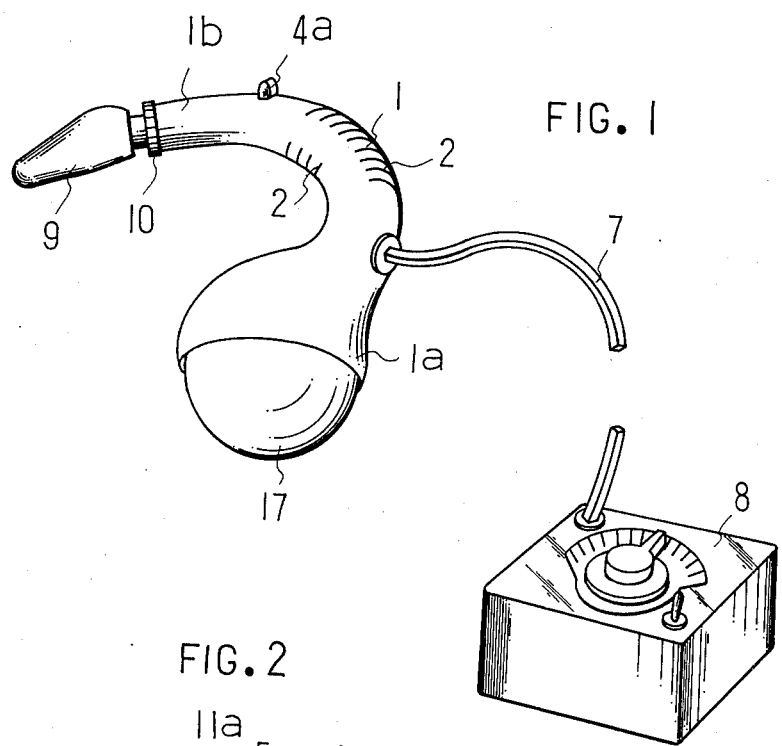
FIG. 1 is a perspective view of the first embodiment of this invention.
Figure 2:
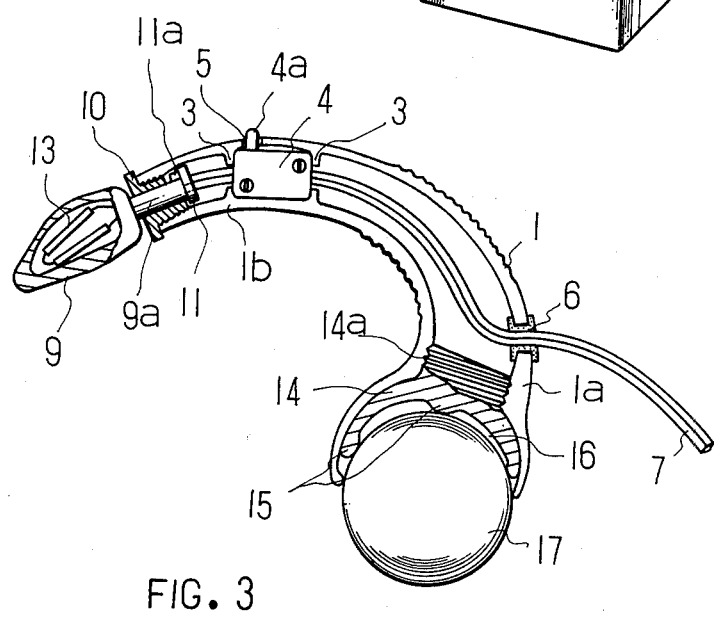
FIG. 2 is a sectional view of the embodiment.
Figure 3:
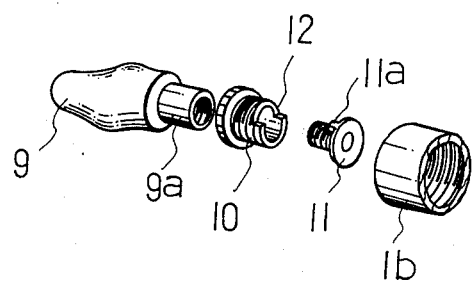
FIG. 3 shows a massaging part, which is broken up, of the embodiment.

Referring to FIGS. 1 to 4, a massaging instrument is provided with a grip 1 of a synthetic resin an end of which is expanded. The middle portion of the grip 1 is notched as shown by a numeral 2 for gripping. The grip 1 is assembled from two longitudinally divided parts. In the grip 1, a switch 4 is incorporated, a button of which projects from the outer surface of the grip 1 through a hole 5. A cord 7 connected to the switch 4 is connected to a variable transformer 8 through a hole 6 provided at a portion of the grip 1 neighboring to the expanded end 1a. On another end 1b of the grip 1, a hot massaging part 9 is mounted a tubular screw 9a into which a screw 11 is screwed. As shown in FIG. 3, an end of a screw 10 is partially cut out as shown by a numeral 12. A projection 11a on the screw 11 is located in a room provided by the cut-out portion 12 when parts 9, 10 and 11 are assembled, whereby the massaging part 9 is rotatable relatively to the grip 1. A heating wire 13 is incorporated in the massaging part 9. When a woman pushes the button 4, electric current is supplied to the wire to heat it. To the expanded end 1a of the grip 1, a permanent magnet 14 is mounted with a screw 14a. The magnet 14 has a substantially spherical inner face 16 and a plurality of projections 15 to form a seat for a sphere 17. Since the sphere 17 is also of a magnetic material, the sphere is fastened onto the magnet 14. The sphere 17 is of a magnetic material having a relatively large specific heat and therefore remains cold for a relatively long time when the sphere 17 is cooled, whereby the sphere 17 acts as a cold massaging part.

The aforesaid massaging instrument is used as explained hereinafter.

By operating the variable transformer, the voltage applied to the heating wire 13 is adjusted to heat the hot massaging part 9 to a temperature of about 40° to 60° C.

On the other hand, the sphere 17 is cooled in an icebox or an electric refrigerator to a temperature of about 4° C and then attached to the magnet 14. The hot massaging part 9 and the cold massaging part 17 are alternatively applied to human skins to conduct massage. The inventors carried out massage for 5 minutes at two times, that is, at morning and evening every day. When such massaging was continiued for 2 weeks, skins became surprisingly beautiful. Such performance is thought to be caused by combined action of thermal stimulation due to large difference in temperature and magnetic energy, which activate cells constituting skins and amplify metabolism.

Figure 4:
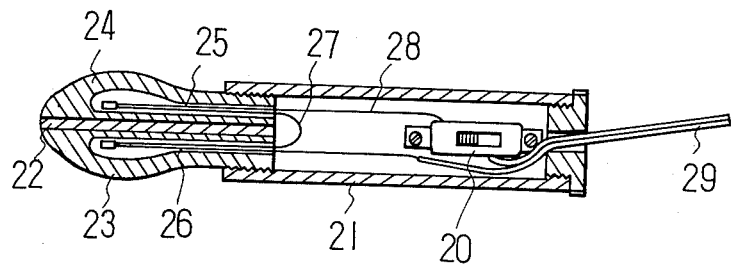
FIG. 4 is a sectional view of the second embodiment of this invention.

The second embodiment of this invention is shown in FIG. 4. In FIG. 4, a sliding switch 20 is provided in a grip 21. A hot massaging part 24 and a cold massaging part 23 is mounted to the left end of the grip 21 with interposition of a thermally isolating plate 22. Two metallic wires 25 and 26 which constitute a thermo couple which is known as having Peltier effect are incorporated in the massaging parts. The metallic wires 25 and 26 are connected to each other at 27 and to a direct current source, which is not shown, through the switch 20 and a cord 29.

It will be understood that this embodiment also has the same massaging effect as that of the first embodiment. Further, at least one of the massaging parts 23 and 24 can be composed of a magnet, whereby more massaging performance can be attained by magnetic energy. Still further, the thermo couple can be composed of a semiconductor.

Figure 5:
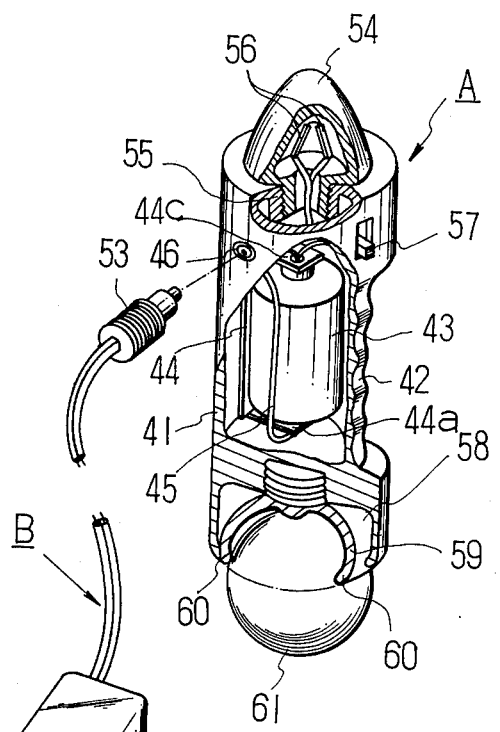
FIG. 5 is a perspective view of the third embodiment, which is partialy broken, of this invention.

The third embodiment of this invention is shown in FIG. 5. In FIG. 5, a massaging instrument A is connected with a charger B. The massaging instrument is provided with a grip 41 which is composed of a molded and synthetic resin having heat resistance. The outer surface of the grip 41 is shaped so as to fit a hand as shown by a numeral 42. In the grip 41, a housing for a storage battery 43 such as a nikel-cadmium cell is provided. Electrodes 44a and 44b on the housing 44 are connected to a soket 6 with a cord 45, which socket 46 appears on the outer surface of the grip 41. The charger B comprises a charger box 48 and plugs 47 and 53. The plug 47 can be connected to a regular electric source.

Figure 6:
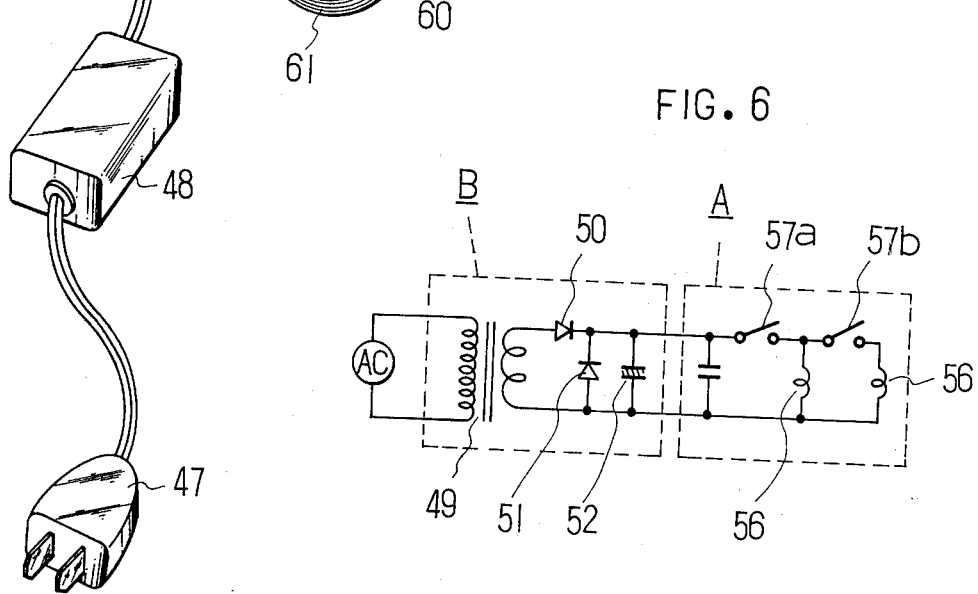
FIG. 6 shows an electric circuit used in the third embodiment.

In the charger box 48, a reduction transformer 49, zener diodes 50 and 51 which is connected to the secondary coil of the transformer 49 and a capacitor 52 which is connected parallely with the diode 51 as shown in FIG. 6. The output terminals of the rectifying circuit composed of the zener diodes 50 and 51 and capacitor 52 are connected to the plug 53. A hot massaging part which has a cone-like shape is mounted to the grip 51 with a screw 55. In the massaging part 54, two heating wires 56 are provided.

The heating wires 56 are connected to the storage battery 43 through a sliding switch 57. The sliding switch 57 is provided with two switch elements 57a and 57b and can be switched to three modes. At two of the modes, the switch elements 57a and 57b are individually closed. At the lower end (in FIG. 5) of the grip 41, an open room 48 is provided. A permanent magnet 49 having a half sphere-shape is mounted to the grip 41 in the room 58. The magnet 59 has a plularity of projections 60 to form a seat for a sphere 61. The sphere 61 is of a strongly magnetic material and used as a cold massaging part. The massaging part A is used as follows. The storage battery 43 is charged by the charger B. And then the sliding switch 57 is operated to heat the hot massaging part so that the temperature of the surface of the massaging part 54 became about 40° to 60° C.

On the other hand, the sphere 61 is stored in an ice box or an electric refrigerator to cool the sphere 61 to a temperature of about 4° C and then the sphere 61 is attached to the magnet 59. The hot massaging part 54 and the cold massaging part 61 are alternatively applied to human skins to massage the skin. Also by this embodiment, excellent massaging effect was confirmed when the massaging was continiued for 2 weeks with two times at morning and evening every day.

According to this invention, more effective massage is attained than that according to prior art massaging instruments, because stronger thermal stimulation is given to human skins with more temperature difference than these of prior art massaging methods. By such thermal stimulation, human skins are effectively beautified. Further, according to this invention, troublesome procedures such as the preparation of hot water become needless and sufficient massaging effect is attained by conducting massage at only or two times every day.

Still further, a thermal type massaging instrument according to this invention can be used without attachment of any auxiliary parts such as a cord and therefore the instrument is very conveniently used.

What is claimed is:

1. A massaging instrument comprising a grippable support member, a first massaging part which is supported by said member and heated to give hot thermal stimulation to human skins, and a second massaging part which is supported by said member and cooled to give cold thermal stimulation to human skins, wherein said member has a permanent magnet and said second massaging part is composed of a magnetic material, whereby said second massaging part is detachably mounted to said member.

2. A massaging instrument according to claim 1, wherein said second massaging part is composed of a material having large specific heat.

3. A massaging instrument comprising a grippable support member, a first massaging part mounted to one end of said member, a shell-like shaped seat of a permanent magnet mounted to another end of said member, a sphere-shaped second massaging part of a magnetic material attached to said seat, a means for heating said first massaging part which is located in said first massaging part, means for supplying electric current to said heating means and said supplying means having a switch which is incorporated in said member.

4. A massaging instrument comprising a grippable support member, a first massaging part, a second massaging part, said massaging parts being mounted to one end of said member, a thermally isolating plate interposed between said first and second massaging parts, a thermo couple which comprises two wires each of which is respectively incorporated in said first and second massaging parts and a means for supplying electric current to said thermo couple.

* * * * *